United States Patent [19]
Boinot et al.

[11] Patent Number: 5,277,669
[45] Date of Patent: Jan. 11, 1994

[54] APPARATUS FOR THE REDUCTION/INCREASE IN SPEED OF A MICROMOTOR AND MICROMOTOR EQUIPPED THEREWITH

[75] Inventors: Claude J. Boinot, Chatillon Le Duc; Bernard Lacour, Besancon, both of France

[73] Assignee: Micro Mega SA, Besancon, France

[21] Appl. No.: 909,774

[22] Filed: Jul. 7, 1992

[30] Foreign Application Priority Data

Jul. 8, 1991 [FR] France ................. 91 08710

[51] Int. Cl.$^5$ ............................................. F16H 37/06
[52] U.S. Cl. ........................................ 475/5; 475/296; 475/331
[58] Field of Search ................ 475/5, 295, 296, 298, 475/330, 331, 196, 169, 170

[56] References Cited

U.S. PATENT DOCUMENTS

| | | | |
|---|---|---|---|
| 3,631,742 | 1/1972 | Hoffmeister | 475/196 OR |
| 4,040,311 | 8/1977 | Page, Jr. et al. | 475/298 X |
| 4,063,470 | 12/1977 | Kelbel | 475/295 X |
| 4,306,865 | 12/1981 | Leonard | 475/331 X |
| 4,344,746 | 8/1982 | Leonard | |
| 4,617,837 | 10/1986 | Kataoka et al. | 475/296 X |

FOREIGN PATENT DOCUMENTS

2454513 11/1980 France .

*Primary Examiner*—Leslie A. Braun
*Assistant Examiner*—Daniel Wittels
*Attorney, Agent, or Firm*—Weiser & Associates

[57] ABSTRACT

A device for stepping down and/or stepping up the speed of rotation of a motor element, such as a dental micromotor, includes two toothed pinions with common axes of rotation and which are mounted in a support piece. The support piece can turn through an angle ($\alpha$) with respect to the body o the motor element about an axis (A) parallel with an axis (o) of the input pinion of the device and offset with respect to the axis (o) by a distance (OA). The axis (A) is further offset with respect to the axis (O') of rotation of the output pinion by a distance (AO') equal to the distance (OA). As a result, in a first position, the axis (O') is merged with the axis (O), and a first one of the pinions (or a crown wheel) is meshed with elements upstream of the kinematic chain. In a second position, following rotation of the support piece through a defined angle ($\alpha$), the first one of the pinions is disengaged and a second one of the pinions (or a crown wheel(), is, in turn, meshed with the elements upstream of the kinematic chain.

14 Claims, 1 Drawing Sheet

APPARATUS FOR THE REDUCTION/INCREASE IN SPEED OF A MICROMOTOR AND MICROMOTOR EQUIPPED THEREWITH

BACKGROUND OF THE INVENTION

This invention relates to devices for stepping up or stepping down the speed of rotation of a micromotor, particularly micromotors for dental use, whether electric or pneumatic. More particularly, the present invention relates to a device for providing two different speed ratios at the motor's output, and to handpieces and micromotors fitted with such a device. Although the disclosed device is primarily intended for motors it is also applicable to other devices calling for similar speed control.

Dental practice often requires very different ranges of rotational speed for the tool (e.g., a drill) depending on the operation to be performed. For example, for drilling operations, the speed of rotation will correspond to the maximum speed of the motor, whereas for prophylactic operations, the necessary speed will correspond to the minimum speed of the motor.

It is of course possible to cause the speed of an electric motor to vary by adjusting the supply device, and to vary the speed of a pneumatic motor by a device such as that described in French Patent 2,454,513. The disadvantage is that in all cases, and in particular for pneumatic motors, the torque characteristic falls away considerably at low speed. This disadvantage can be palliated by placing a straight or reverse-angled handpiece on the motor. This ensures a speed reduction so that the motor can turn at an acceptable speed. However, the practitioner is then constrained to have two types of handpieces.

SUMMARY OF THE INVENTION

The primary object of the present invention is therefore to provide a device which permits the practitioner to employ two distinct speed ranges, one termed low speed and the other termed high speed, using only a single handpiece.

It is another object of the present invention to provide a device having such a capability which can be placed directly on the motor, and which is even capable of being integral with it.

These and other objects are achieved in accordance with the present invention by a device for stepping down and/or stepping up the rotational speed of a motor element, such as a dental micromotor, which device is generally comprised of two toothed pinions (i.e., output pinions or crown wheels) having common axes of rotation and securely attached to the output shaft of the motor element. The two toothed pinions are mounted in a support piece so that within the support piece, they can turn through an angle ($\alpha$) with respect to the body of the motor element about an axis (A) parallel to the axis (O) of the input pinion of the device, and offset from this axis by a distance (OA). The axis (A) is itself offset from the axis (O') of the output pinion by a distance (AO') equal to the distance (OA) so that, in a given position, the axis (O') is merged with the axis (O). In this position, one of the pinions (or crown wheels) is meshed with upstream elements of the kinematic chain. Following a rotation ($\alpha$) of the support piece, this pinion is disengaged and the remaining pinion (or crown wheel) is, in turn, meshed with the upstream elements of the kinematic chain.

Transmission of movement is obtained through a triple pinion provided on a secondary shaft and having teeth which are engaged respectively with the input pinion and the output pinion. In position corresponding to a rotation through the angle ($\alpha$) with respect to the initial position, the output pinion is disengaged from the teeth of the triple pinion (with which it was meshed) and a toothed crown wheel is brought into engagement with a tertiary pinion for rotating the output shaft.

For further detail regarding the present invention, reference is made to the following description, based on the accompanying drawings.

DESCRIPTION OF A PREFERRED EMBODIMENT

Figure 1A:
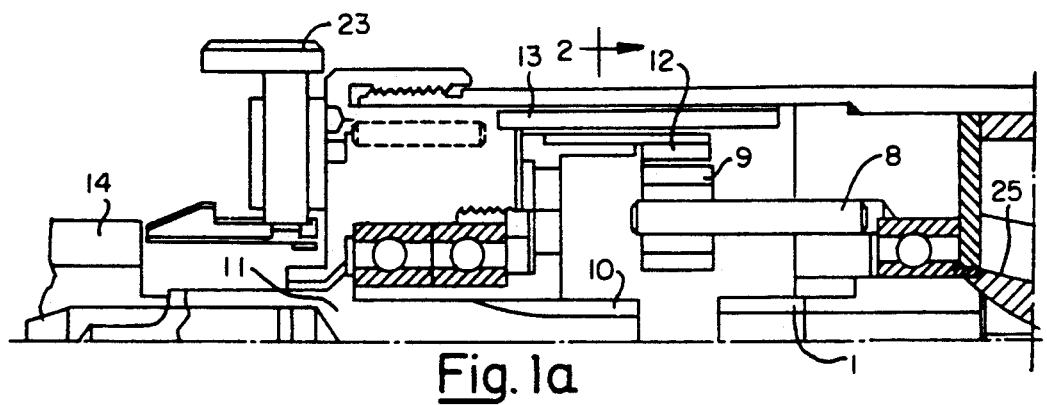
FIGS. 1a and 1b are longitudinal cross-sectional views of the device of the present invention.
Figure 1B:
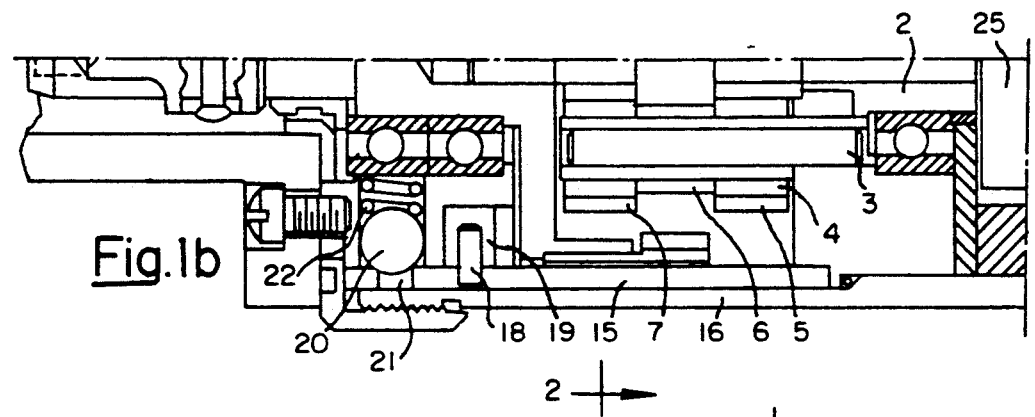

FIGS. 1a and 1b show, in longitudinal cross-section, a device produced according to the present invention. To this end, an input pinion 1 is securely attached to the output shaft 2 of a motor element. A secondary shaft 3 is mounted parallel to the output shaft 2 and supports a triple pinion 4 having teeth 5, 6 and 7. The teeth 5 are meshed with the input pinion 1. A tertiary shaft 8 is also mounted parallel to the output shaft 2, and supports a tertiary pinion 9 which is meshed with the teeth 6 of the triple pinion 4. Both an output pinion 10 and a toothed crown wheel 12 are securely attached to the output shaft 11.

The foregoing components are mounted in a barrel 13 which is securely attached to a coupling sleeve 14. The coupling sleeve 14 can advantageously conform, for example, to ISO Standard 3964. The assembly 13, 14 is capable of turning through an angle ($\alpha$) with respect to a sleeve 15 which is preferably integral with the body 16 of the motor.

Figure 2:
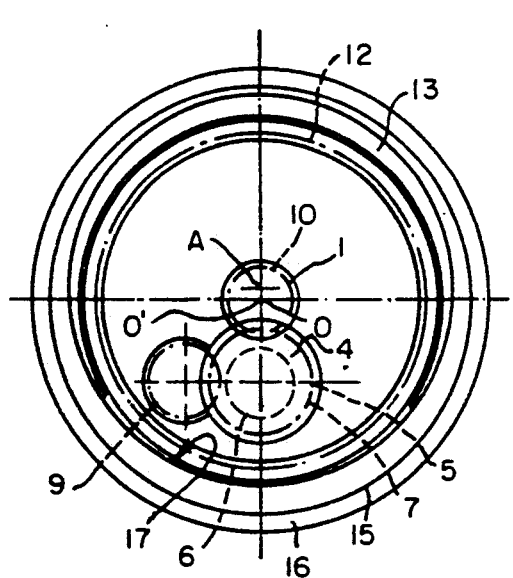
FIG. 2 is a cross-sectional view of the device of FIG. 1, taken along the line 2—2, in a 1/1 ratio (stepped up) position.
Figure 3:
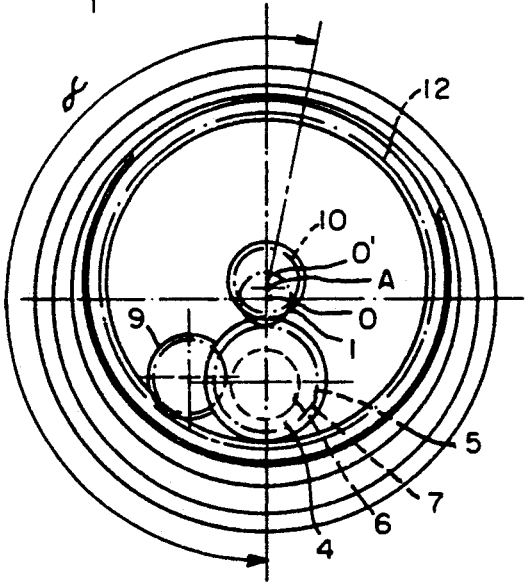
FIG. 3 is a cross-sectional view of the device of FIG. 1, taken along the line 2—2 in a ¼ ratio (stepped down) position.

Referring now to FIGS. 2 and 3, and in order to facilitate comprehension, the tertiary pinion 9 and the triple pinion 4 are shown in cross-section relative to the output pinion 10 and the crown wheel 12. Meshed engagement of these components is achieved, as shown in FIGS. 2 and 3, depending upon the disposition of these elements and the desired operation (speed of rotation) of the device. It will be noted that in these Figures, the bore 17 of the sleeve 15 has an axis passing through a point (A), that the outer diameter of the barrel 13 has an axis passing through the point (A), and that the outer diameter of the sleeve 15 passes through a point (O) which corresponds to the axis of the input pinion 1.

In the position of FIG. 2, the axis (O') of the output shaft 11 is found to coincide with the axis (O) of the input pinion 1. In this position, the output pinion 10 is meshed with the teeth 7 of the triple pinion 4. As previously indicated, the teeth 5 are permanently meshed with the input pinion 1. This leads to a transmission ratio:

$$R_1 = \frac{N1}{N5} \times \frac{N7}{N10},$$

where
N1=number of teeth of the input pinion 1,
N5=number of teeth 5,
N7=number of teeth 7, and
N10=number of teeth of the output pinion 10.

Referring next to FIG. 3, when the barrel 13 is caused to turn through an angle (α), the barrel 13 turns with the coupling sleeve 14. The output shaft II (and accordingly, the axis of the output pinion O') moves along an arc of a circle to assume the position of FIG. 3, which results from the various eccentricities of the bores and the outer diameters of the barrel 13 and the sleeve 15. In this case, the output pinion 10 is no longer meshed with the teeth 7. Rather, the tertiary pinion 9 is brought into a position which meshes with the crown wheel 12. This leads to a transmission ratio:

$$R_2 = \frac{N1}{N5} \times \frac{N6}{N9} \times \frac{N9}{N12} = \frac{N1}{N5} \times \frac{N6}{N12}.$$

It will be noted that the tertiary pinion (N9) plays no part in the transmission ratio $R_2$. Rather, its sole purpose is to maintain a direction of rotation for the output which corresponds to that of the arrangement shown in FIG. 2. Thus, the device may be constructed with no tertiary pinion if a change in direction of rotation is desired between the two operating positions.

Rotation of the barrel 13 relative to the sleeve 15 may be regulated by providing the sleeve with a radial pin 18 which extends into a circular groove 19 formed in the barrel 13. The pin then serves as a mechanical stop for defining extreme positions of rotation through the angle (α), which preferably exceeds 180°. Such extreme positions of rotation may be maintained by a locking device, if desired, such as a ball 20 biased into bores 21 formed in the sleeve 15 for defining extreme positions of rotation under the influence of a spring 22. A push-button release 23 may advantageously be provided for operating the device through the angle (α), if desired.

We claim:

1. A device for changing the rotation speed of a motor element, comprising an input pinion for receiving a rotating shaft of the motor element, an output for rotating a rotating element, and two toothed pinion means having common axes of rotation and mounted in a support piece, wherein the support piece turns through a defined angle about a first axis parallel to a second axis defined by the input pinion, and offset with respect to the second axis by a first distance, and wherein the first axis is further offset with respect to a third axis defined by the output by a second distance equal to the first distance, so that in a first position of the support piece, the third axis is merged with the second axial and a first one of the toothed pinion means is engaged, and so that in a second position of the support piece, disposed at the defined angle relative to the first position, the first one of the toothed pinion means is not engaged and a second one of the toothed pinion means is engaged.

2. The decide of claim 1 wherein the input pinion is mounted on an output shaft of the motor element, and which further includes:
   a secondary shaft parallel with e output shaft of the motor element and supporting a triple pinion having first, second and third teeth, wherein the first teeth are meshed with the input pinion;
   a tertiary shaft parallel with the output shaft of the motor element and supporting a tertiary pinion meshed with the second teeth of the triple pinion;
   an output pinion having an axis of rotation, for meshing with the third teeth of the triple pinion and securely attached to the output shaft; and
   a toothed crown wheel having an axis of rotation merged with the axis of rotation of the output pinion and securely attached to the output shaft, and capable of rotation through the defined angle to mesh with the tertiary pinion.

3. The device of claim 2 wherein the support piece comprises a bore having an outer diameter which is eccentric by a third distance corresponding to the first distance and which is positioned for rotation within a fixed bore which is eccentric relative to the axis of the input pinion by a fourth distance corresponding of the first distance so that in a first position, the third distance and the fourth distance are placed in opposition and the output pinion is coaxial with the input pinion and meshed with the first one of the toothed pinion means, and so that in a second position, following rotation of the support piece through the defined angle, the output pinion ceases to mesh with the first one of the toothed pinion means and meshes with the second one of the toothed pinion means.

4. The device of the claim 1 in combination with a device for coupling a dental handpiece.

5. The device of claim 4 wherein the coupling device is securely attached to the support piece.

6. The device of claim 5 wherein the coupling device includes push button means for operating the device for changing the rotation speed of the motor element through the defined angle.

7. The device of claim 4 wherein the coupling device is in accordance with ISO Standard 3964.

8. The device of claim 1 wherein the device further includes means for locking extreme positions of rotation through the defined angle.

9. The device of claim 8 wherein the locking means includes a ball based radially by a spring attached of the support piece, wherein the ball engages bores formed in the device.

10. The device of claim 2 wherein the device further includes mechanical stops at extreme positions of rotation through the defined angle.

11. The device of claim 10 wherein the mechanical stops are defined by a radial pin fixed for interacting with a circular groove formed in the device.

12. The device of claim 1 wherein the angle defined is greater than 180°.

13. A micromotor comprising a motor element and a device for changing the rotation speed of the motor element including an input pinion for receiving a rotating shaft of the motor element, an output for rotating a rotating element, and two toothed pinion means having common axes of rotation and mounted in a support piece, wherein the support piece turns through a defined angle about a first axis parallel to a second axis defined by the input pinion, and offset with respect to the second axis by a first distance, and wherein the first axis is further offset with respect to a third axis defined by the output by a second distance equal to the first distance, so that in a first position of the support piece, the third axis is merged with the second axis and a first one of the toothed pinion means is engaged and so that in a second position of the support piece, disposed a the defined angle relative to the first position, the first one of the toothed pinion means is not engaged and a second one of the toothed pinion means is engaged.

14. A dental handpiece comprising a motor element and a device for changing the rotation speed of the motor element including an input pinion for receiving a rotating shaft of the motor element, an output for rotating a rotating element, and two toothed pinion means having common axes of rotation and mounted in a support piece, wherein the support piece turns through a defined angle about a first axis parallel to a second axis defined by the input pinion, and offset with respect to the second axis by a first distance, and wherein the first axis is further offset with respect to a third axis defined by the output by a second distance equal to the first distance, so that in a first position of the support piece, the third axis is merged with the second axis and a first one of the toothed pinion means is engaged, and so that in a second position of the support piece, disposed at the defined angle relative to the first position, the first one of the toothed pinion means is not engaged and a second one of the toothed pinion means is engaged.

* * * * *